United States Patent [19]

Parce et al.

[11] Patent Number: 5,395,503
[45] Date of Patent: * Mar. 7, 1995

[54] ZERO VOLUME ELECTROCHEMICAL CELL

[75] Inventors: John W. Parce, Palo Alto; Robert F. Zuk, Burlingame, both of Calif.

[73] Assignee: Molecular Devices Corporation, Sunnyvale, Calif.

[ * ] Notice: The portion of the term of this patent subsequent to Mar. 27, 2007 has been disclaimed.

[21] Appl. No.: 129,541

[22] Filed: Sep. 29, 1993

Related U.S. Application Data

[63] Continuation of Ser. No. 804,122, Dec. 6, 1991, abandoned, which is a continuation of Ser. No. 437,741, Nov. 16, 1989, abandoned, which is a continuation of Ser. No. 876,925, Jun. 20, 1986, Pat. No. 4,915,812.

[51] Int. Cl.[6] ............................................. G01N 27/327
[52] U.S. Cl. ........................... 204/403; 204/153.12; 204/222; 204/225; 204/400; 204/409; 204/415; 204/416
[58] Field of Search ............... 204/153.1, 153.12, 400, 204/403, 409, 415, 416, 418, 419, 225, 222

[56] References Cited

U.S. PATENT DOCUMENTS

| | | | |
|---|---|---|---|
| 2,503,337 | 4/1950 | Hirsh et al. | 204/225 |
| 3,024,172 | 3/1962 | McLain et al. | 204/225 |
| 3,403,081 | 9/1968 | Rohrback et al. | 204/403 |
| 3,420,765 | 1/1969 | Uhrenholdt | 204/400 |
| 3,503,861 | 3/1970 | Volpe | 204/415 |
| 3,926,765 | 12/1975 | Haddad | 204/435 |
| 4,184,935 | 1/1980 | Schindler et al. | 204/418 |
| 4,216,065 | 8/1980 | Rechnitz et al. | 204/153.12 |
| 4,271,002 | 6/1981 | Hawkins | 204/418 |
| 4,468,271 | 8/1984 | Pierson | 204/418 |
| 4,490,236 | 12/1984 | Petty | 204/409 |
| 4,776,944 | 10/1988 | Janata et al. | 204/418 |
| 4,911,794 | 3/1990 | Parce et al. | 204/415 |
| 4,915,812 | 4/1990 | Parce et al. | 204/403 |

*Primary Examiner*—T. Tung
*Attorney, Agent, or Firm*—Allegretti & Witcoff, Ltd.

[57] ABSTRACT

Methods and apparatuses are described for determining the presence of an analyte in a sample suspected of containing the analyte. The method comprises contacting a concentrate of a determinable element capable of being detected by means of a semiconductive electrode with the electrode in the presence of a relatively large volume of an assay medium. The determinable element is present in the concentrate in the amount related to the amount of analyte present in the sample. The volume of the medium in diffusive communication with the concentrate is then reduced and the determinable element is detected by means of the effect that the determinable element has on the semiconductive electrode.

3 Claims, 5 Drawing Sheets

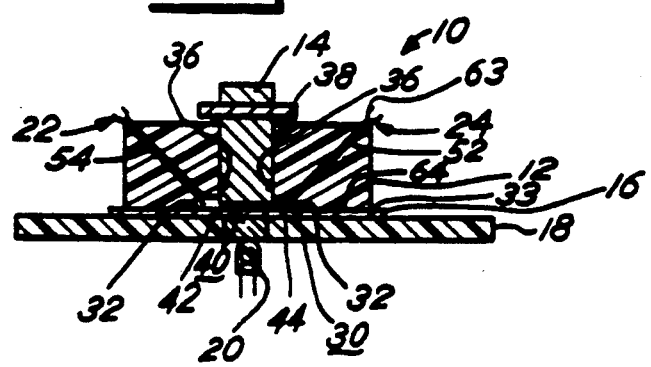
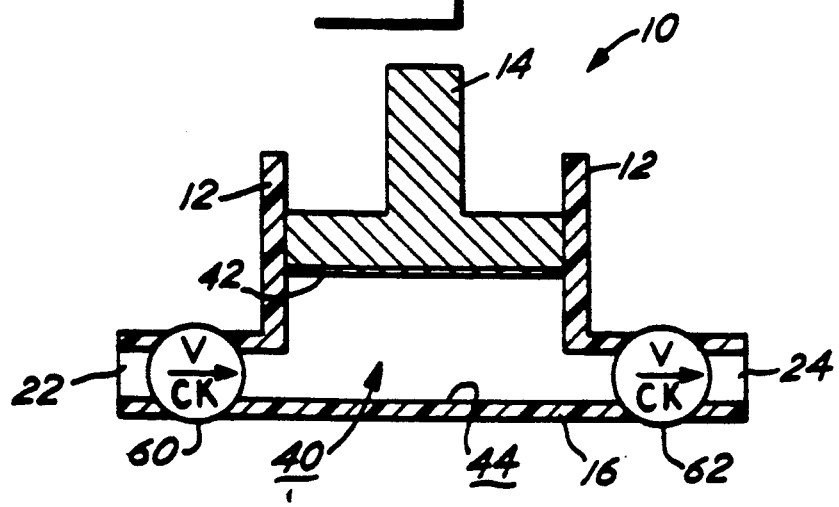
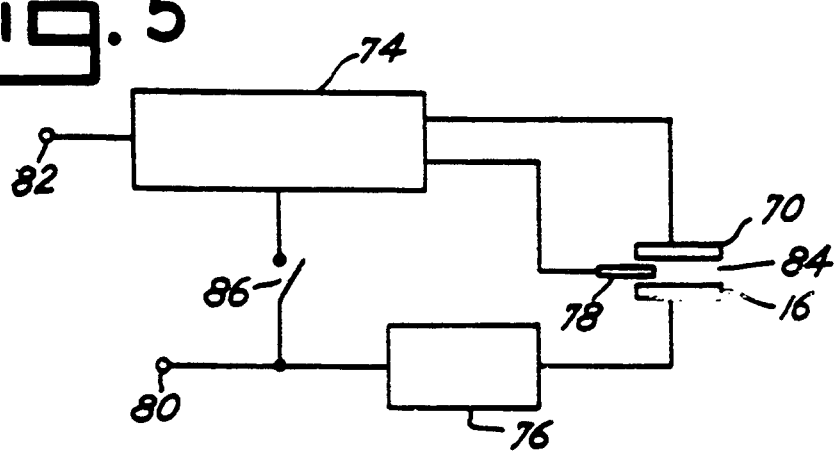

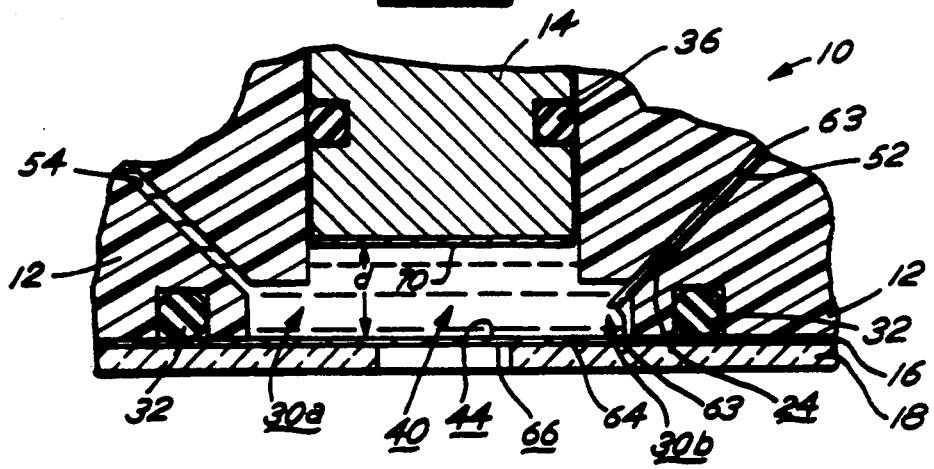
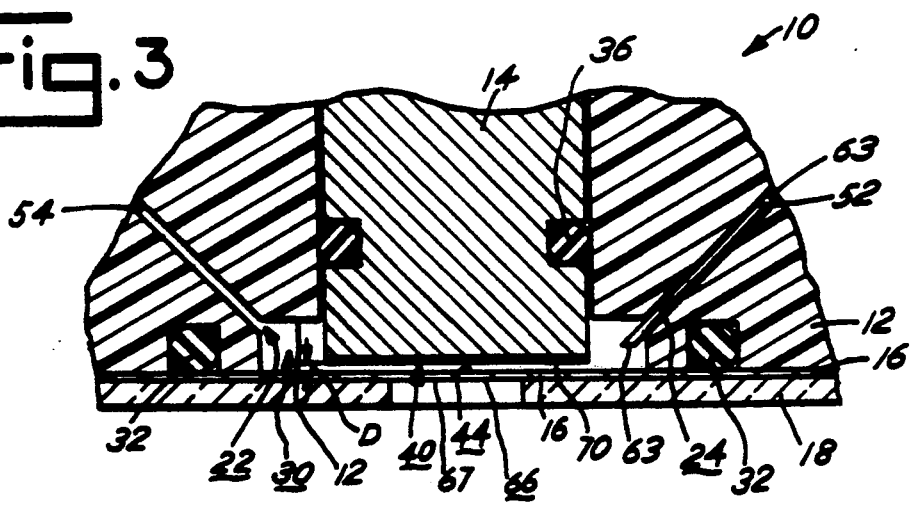
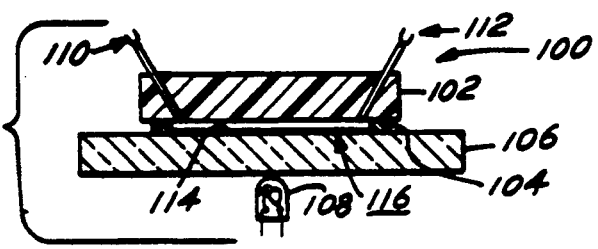
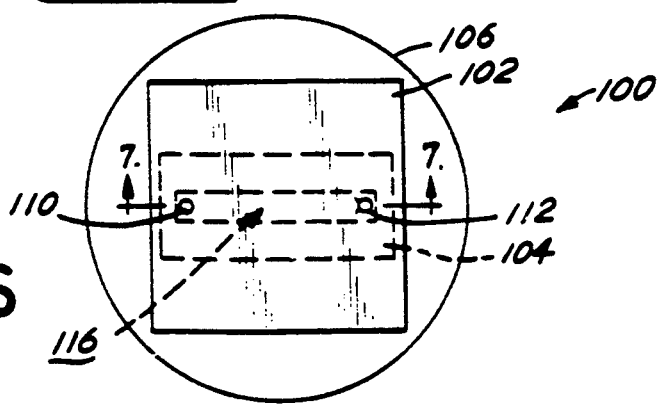

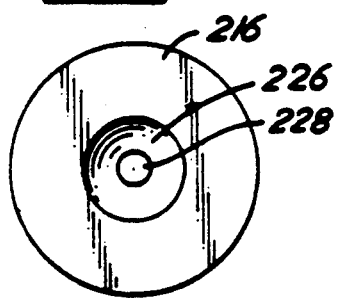 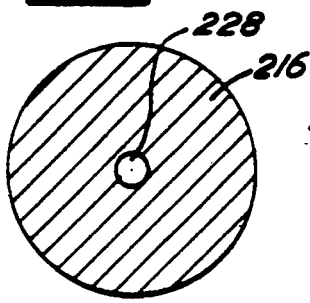 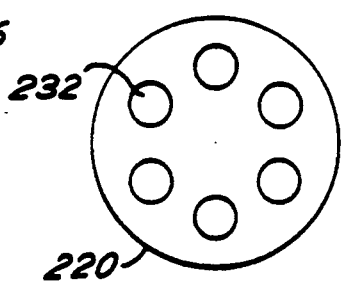
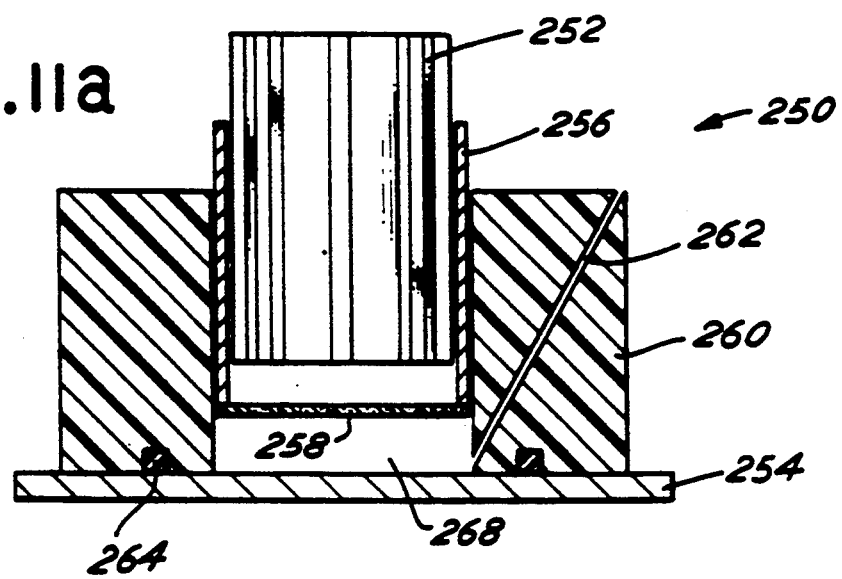
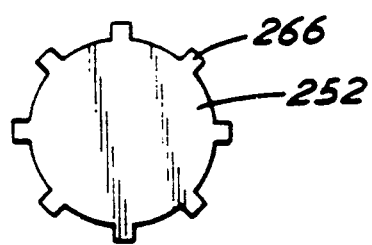

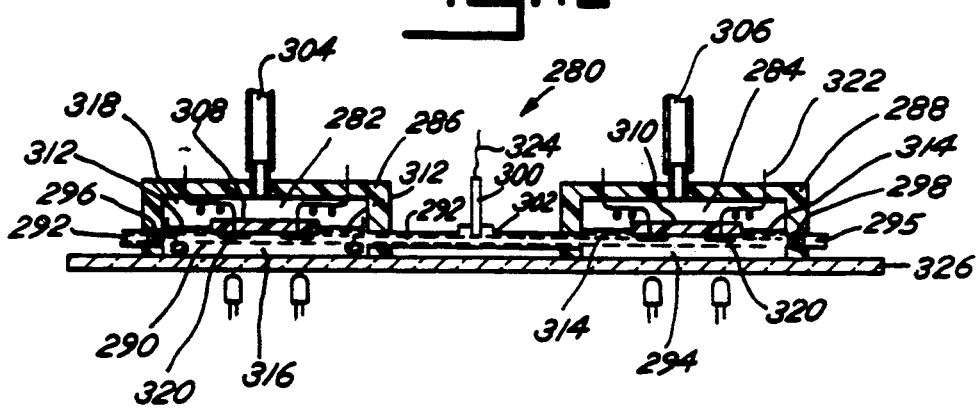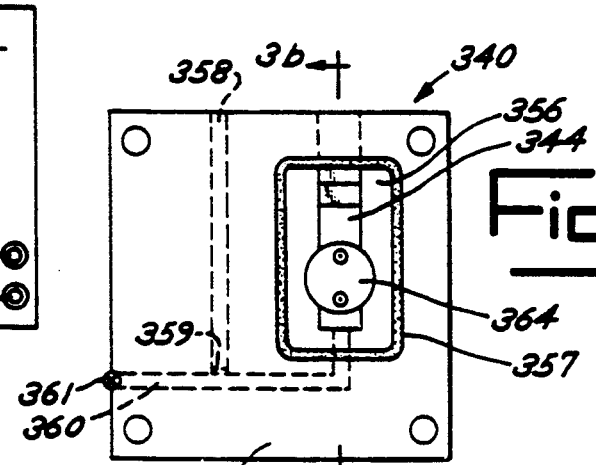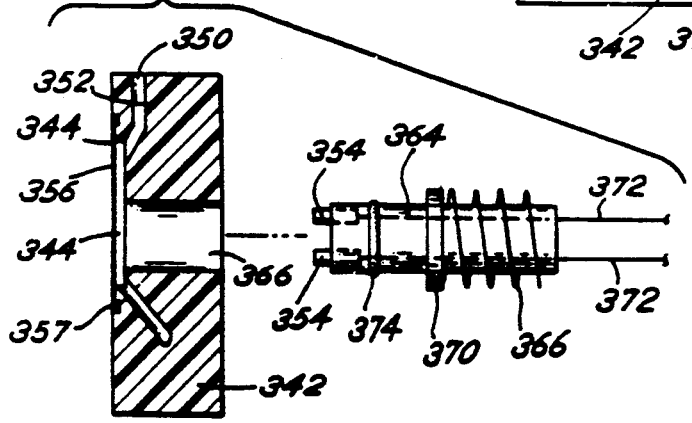

ZERO VOLUME ELECTROCHEMICAL CELL

This is a continuation of application Ser. No. 07/804,122, filed Dec. 6, 1991, now abandoned, which is a continuation of Ser. No. 07/437,741, filed Nov. 16, 1989, now abandoned, which is a continuation of Ser. No. 06/876,925, filed Jun. 20, 1986, now U.S. Pat. No. 4,915,812.

BACKGROUND OF THE INVENTION

The detection of the presence of a material and/or its amount in a particular environment becomes increasingly important in a society which seeks to monitor or manipulate its environment. Despite the long history of developing devices for measurement of various materials in liquid or other fluid media, there still remains ample opportunity for improvements in the sensitivity, efficiency, economy, and ease of use. Among such devices and measurement methods, various electrochemical devices and methods have shown potential for increased specificity and flexibility of measurement.

In one type of electrochemical device, the electrical signal of interest is due primarily to the interactions between the electrode surface and the solution of interest in a small region very near the electrode surface ("surface region"). In these devices, the portion of the solution ("bulk solution"), which is more than a short distance from the working electrode surface, does not contribute to and may interfere with the reactions and/or interactions of interest. One of the problems encountered in the use of such devices for measurement of analytes in fluid media, particularly biological media, is that the magnitude of the interaction of the components of the solution with the electrode and/or the effective rates of reactions in the solutions, as measured with the electrode, may be mediated and/or diminished by the interactions between the bulk solution and the surface region of solution. Such effects may arise by diffusion of surface-active species into the bulk solution and/or quenching of the surface reaction due to interaction with the bulk solution. For example, where the property to be measured is pH, the generally large buffering capacity of the bulk solution moderates the change in pH near the electrode surface, as well as the rate of change in pH, so that the magnitude of the observed electrode signal is substantially reduced and/or the effective responsiveness of the electrode to time-dependent processes is reduced.

To avoid such effects and to limit the solution to a volume which substantially completely interacts with the electrode over very short periods of time, it would be desirable to provide devices which allow for reactions of interest in relatively large volumes while measuring the result with a volume with which the electrode may effectively communicate. Such a feature would be preferentially selective of the reaction and/or interaction occurring between the solution and the electrode surface, and minimize interferences, damping effects, and the like between the surface region of the solution and the bulk solution.

Description of the Relevant Literature

References of interest include U.S. Pat. Nos. 4,020,830 to Johnson, et al.; 3,975,238 to Bean, et al.; 4.238,757 to Schenck; 4,486,272 to Fujihira; 4,293,310 to Weber; and 4,444,892 to Malmros; and International Patent Publications Nos. WO83/02669 and WO85/04018. See also Experimental Electrochemistry for Electrochemists, Sawyer and Roberts, Wiley-Interscience. pp. 350–353.

SUMMARY OF THE INVENTION

Apparatus and methods are provided for measuring, in an electrochemical cell, an analyte in a fluid medium. The apparatus employs a cell having a working and a controlling electrode and, preferably, a reference electrode. The cell also includes means for varying the volume of the cell, means for introducing and removing fluid from the cell, and, where the working electrode which is used is a photo-responsive electrode, illumination means for irradiating a photo-responsive surface of the working electrode.

In the preferred embodiment of the invention, the working and controlling electrodes comprise or are mounted to or coated on first and second elements in displaceable relationship.

The volume of the cell can be varied from a relatively large volume for convenient introduction and removal of the fluid medium, as well as for reaction between relatively large amounts of one or more dilute reactants to a small volume during measurement in which the fluid medium is distributed in a reproducibly thin layer at the surface of the working electrode. The layer of fluid is, during the measurement, sufficiently thin that the interference effects of bulk solution on the electrode response are substantially reduced or eliminated and the small volume of fluid used is utilized as efficiently as possible.

The methods find potential application with specific binding pairs of species, where one of the pair is bound to a solid support, and is concentrated in the vicinity of the working electrode surface during measurement. The other member of the pair will normally react with its homologous member and becomes bound to the solid support. The reactions between the bound and unbound members can be performed in a relatively large volume; thereafter, most of the fluid can be evacuated from the cell and the electrochemical measurement made in the absence of most of the assay medium. The method finds particular application where the bulk medium tends to react with the agent for surface modification or unduly dilute the agent.

BRIEF DESCRIPTION OF THE DRAWINGS

FIG. 1 is a schematic cross-sectional view of a first exemplary electrochemical cell according to the invention.

FIG. 2 is a cross-sectional detail view of the first exemplary electrochemical cell, showing the plunger in an "up" position.

FIG. 3 is a cross-sectional detail view of the first exemplary electrochemical cell, showing the plunger in a "down" position.

FIG. 4 is a detail cross-sectional view of a portion of a modified version of the first exemplary electrochemical cell according to the invention.

FIG. 5 is an exemplary schematic circuit for use with the electrochemical cell according to the invention.

FIG. 6 is a plan view of a second embodiment of the invention.

FIG. 7 is a cross-sectional view of a second embodiment of the invention, taken along section 7—7 of FIG. 6.

FIG. 11 is a diagrammatic view of a rigid filter device, while FIG. 11a is a cross-sectional view of a fluted piston.

FIG. 12 is a diagrammatic view of a diaphragm device, with FIG. 12a a diagrammatic plan view of the diaphragm and electrode support looking upward at the bottom of the diaphragm.

FIG. 13 is a diagrammatic side elevational view of a dipstick reader embodiment, with FIG. 13a being a cross-section view along A—A, FIG. 13b being a diagrammatic view of a piston cylinder and FIG. 13c being a plan view of a dipstick.

DETAILED DESCRIPTION OF THE SPECIFIC EMBODIMENTS

Figure 8:
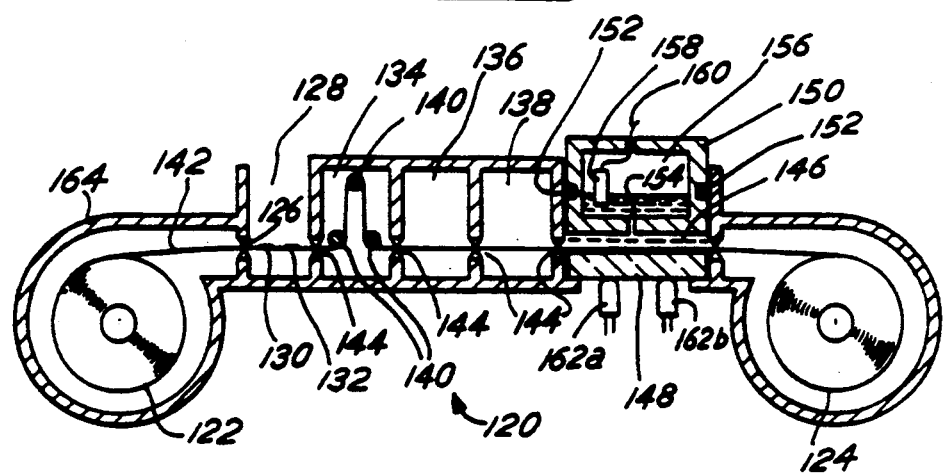
FIG. 8 is a diagrammatic view of a cartridge device.

In accordance with the subject invention, methods and apparatus are provided which allow for carrying out reactions and/or separations in relatively large volumes, while carrying out measurements in relatively small volumes, particularly in situations where one or more components of the large volume have been concentrated in association with a particular surface. For the most part, the methods and apparatus will involve an electrode ("working electrode") which is responsive to changes in a fluid medium, a counter-electrode ("control electode") and a chamber, whose volume can be changed from a relatively large volume to a relatively small volume, where the small volume is in close juxtaposition to the fluid responsive electrode.

The subject apparatus employs surface detection of a substance by means of a semiconductive surface using adjustable opposing electrodes. Usually a catalyst is involved for producing a detectable substance, which catalyst may be bound to either surface or be between the surfaces. The apparatus is then used to detect the change in concentration of the reactant or product of the catalytic reaction.

The methods and apparatus find particular application for the determination of the presence of an analyte. The analyte will usually be one of a specific binding pair—ligand or receptor—where the receptor may be any compound, including proteins, sugars, nucleic acids, or the like, which can specifically bind to another compound, its homologous ligand. In many cases, particularly protein receptors, the receptor will be relatively large compared to the area with which it specifically binds.

The method will normally involve introducing a fluid medium into a chamber, where the chamber is bordered by the working electrode and the control-electrode, with a reference electrode desirably in electrical communication with the fluid in the chamber.

A member of the specific binding pair may be bound to a surface, so as to be in close proximity to the fluid responsive surface at the time of measurement. Thus, the specific binding pair member may be bound to the working electrode, a coating on the working electrode, particles which during the time of measurement will be in close proximity to the fluid responsive surface, the control electrode which may be in close proximity to the working electrode, or the like. The particular manner in which the binding member is positioned adjacent the working electrode is not critical to this invention, so long as the proper spatial relationship is provided and the manner of positioning does not interfere with the reduction in volume of the cell.

The cell is capable of going from a relatively large volume to a relatively small volume, the volume generally varying at least by a factor of 20, more usually at least by a factor of 100, and factors of $10^4$ or more may be achieved. The difference in volume may be achieved by a movable piston or cam, an elastomeric sheet, movable flanges, baffles, pneumatics, or the like. Thus, the apparatus and method allow for a relatively rapid change in volume, where a relatively large volume is introduced into the cell, the particular step of the protocol performed, followed by removal of the major portion of the volume from the cell by reducing the size of the cell. The result of reducing the volume is to reduce the diffusive radius of the signal producing component. Thus, the signal producing component is restrained to remain in the vicinity of the working electrode.

The method can find use with a wide range of ligands and receptors, including aggregations and assemblages of ligands and/or receptors. Thus, haptens, such as synthetically and naturally occurring drugs, hormones, and the like, biocides, including pesticides, herbicides, insecticides, and the like, sugars and polysaccharides, lipids, including fatty acids, fatty acid esters, phosphatides, steroids, e.g. cholesterol, bile acid, etc., proteins, including immunoglobulins, blood factors, lymphokines, interferons, growth factors, transforming factors, oncogenes, etc. nucleic acids, both DNA and RNA, may serve as analytes. Ions may be detected using chelating agents, such as crown ethers. On a larger scale, viroids, viruses, chromosomes, organelles, cells, both prokaryotic and eukaryotic, including pathogens, tumor cells, normal differentiated cells, bacteria, protozoa, metazoa, ciliates, or the like, including lysates thereof or fractions of such lysates, e.g., membrane fragments, may also serve as analytes.

In carrying out the subject method, a component, usually the analyte in the assay medium containing the sample will be segregated from the bulk medium. The segregation may be achieved by specific binding pair complex formation where one of the members of the specific binding pair is bound to a solid support. Alternatively, segregation may be achieved by mechanical means, such as filtration or centrifugation. In some instances, adsorption or chelation might be employed.

With specific binding pair members, one of the members of the specific binding pair will usually be bound to a solid surface, as indicated above. A solution may then be introduced into the cell in its larger volume or expanded state. The fluid will partially or completely fill the cell. The fluid may be relatively dilute for a particular component, which is the reciprocal or homologous specific binding pair member to the member bound to the solid surface. Therefore, by allowing for a reasonable period of incubation, the analyte present in the medium will become concentrated by becoming bound to the surface bound reciprocal member. In this manner, relatively large volumes of dilute solutions of the analyte can be handled, since one provides for concentration of the reciprocal member on a surface which will be in close proximity to the fluid responsive surface. After a sufficient reaction or incubation time, the liquid may be ejected from the cell by reducing the volume of the cell, leaving a thin film of liquid which includes the complex between specific binding members bound to the surface.

Additional sample solutions may be introduced into the cell and the process repeated, or other solutions introduced to provide for washing of non-specific binding reactants to remove background, the addition of additional reagents, or the like. The number of steps in the protocol will vary with the particular protocol employed.

Where a mechanical means is employed for separation, the assay medium may be passed through a membrane in the chamber where the analyte, which may be a part of a particle or aggregation, a cell, virus, or other seperable entity, will be captured by the membrane. The membrane may then be treated with one or more solutions as indicated above, and then pressed against the working electrode by moving one or both of the facing electrodes, so as to bring the two electrodes into close juxtaposition with the membrane sandwiched in between. With centrifugation, the sample can be introduced into the chamber, the device centrifuged with particles being driven against the surface of one of the electrodes.

Alternatively, the assay medium may be contacted with or pass through a membrane which is part of a larger structure, as in a dipstick or wicking stick. The membrane may then be manipulated in accordance with the assay protocol. In a final step, the membrane may be introduced into a chamber with confronting electrodes and an appropriate medium for providing a detectable signal and the membrane pressed against the working electrode by bringing the electrodes together.

The working electrode will be responsive to a change in potential of the medium or other detectable signal. The change in potential may be as a result of a change in pH, a change in concentration of a compound susceptible to oxidation or reduction, or the like. The measured signal may involve light irradiation or a change in the potential of the controlling electrode. Where light is irradiated onto the face of the fluid responsive electrode through the medium or onto the medium, the change in signal may be as a result of the change in absorbtivity or emissivity of the medium.

Numerous protocols exist in the literature involving a wide variety of labels, which provide for different signals. Where labels are employed, these may include catalysts such as enzymes, redox reagents, ionic species, or the like. The particular label will vary depending upon the sensitivity required for the assay, the nature of the fluid responsive electrode, the availability and ease of preparation of reagents, or the like. In some instances, such as cells, no labeling will be required, since the cells may provide for a change in the medium. For example, cells in a nutrient medium will change the pH of the medium, so that the change in the pH may be detected by the fluid responsive electrode.

Illustrative labels are described in U.S. Pat. Nos. 3,791,932; 3,817,837; 3,935,074; 3,998,943; 4,233,402; 4,208,479, 4,233,401; 4,275,149; 4,277,437; and 4,278,300. These patents are incorporated herein by reference, not only for the labels which are disclosed, but also for the protocols which are disclosed.

With specific binding pair members, in carrying out the method, one would provide a chamber having a ligand or receptor bound to a surface, for example, the working electrode surface. One could then introduce the sample, where the reciprocal member of the specific binding pair would become bound to the surface. After sufficient incubation or reaction time, the fluid could be ejected, by bringing the electrodes closer together with only a small volume remaining. One could then separate the electrodes to increase the chamber volume, add a reagent, where the reagent has a label conjugated to the reciprocal binding member to the member bound to the surface or, if the analyte has a plurality of epitopic sites, a labeled reagent comprising a receptor specific for an epitopic site different from the epitopic site by which the analyte is bound to the surface. One could then expel the major portion of the reagent medium, wash if necessary by introducing a wash solution, followed by expulsion of the wash solution, followed by adding a signal producing reagent, if necessary. For example, where an enzyme is the label, one could introduce a substrate for the enzyme. By measuring the change in signal from the medium by means of the working electrode, where the change is related to the amount of analyte, one could determine the amount of analyte in the medium.

Where the analyte is a living cell, one can employ the effect of the living cell on the medium to detect the presence of the cell. For example, one could have antibodies to a particular determinant site of a surface membrane protein or the O-antigen or the like bound to the working electrode. One would introduce the sample into the cell in a relatively large volume, allow the solution to incubate, so that any cells having the appropriate antigens would react with the surface-bound antibody, followed by expulsion of the solution from the measurement cell while reducing the volume to a thin film covering the photoresponsive electrode surface. The cells would then be allowed to metabolize nutrients in the medium, resulting in a change in pH. The change in pH could be detected as indicative of the presence of the particular cell. If desired, the cells could be washed with an appropriate medium before making the measurement, to reduce or eliminate the presence of nonspecific binding. By employing different nutrient media in particular orders, not only could the presence of a pathogenic bacterium be determined, for example, but also the particular species and in some instances the strain without resort to antibodies specific for the strain. Also, as indicated, the cells could be captured by a filter membrane or concentrated by centrifugation to bring the cells in close proximity to an electrode surface.

The apparatus is characterized by having a means for controlling the solution potential and a low resistance means for carrying current, such that the current does not substantially alter the potential of the solution at the site of interest. The current may be an alternating or direct current.

The two modes employed for measuring the effect of the medium on the working electrode will be a photoresponsive mode or a capacitive mode. Depending upon the mode employed to detect the effect of the medium on the surface potential of the semiconductor working electrode, various circuits, electrode configurations, and biasing of the electrodes may be employed where a potential or current may be measured. The circuitry may involve the transfer or absence of transfer of electrons between the assay medium and an electrode.

For the photoresponsive mode, when employing a potentiometric determination in conjunction with a reference electrode, the following configurations may be employed: (1) a conductive control electrode conductively coupled to the electronic circuit; or (2) a capacitive control electrode ($\Psi$) controlled by a reference or separate conductive control electrode. In the second embodiment, where a conductive control electrode is in contact with the medium it may be connected through a capacitor to a control driver, e.g., potentiostat or to ground. Where a conductive control electrode in contact with the medium has a thin insulating surface layer, the conductive electrode may be connected directly to a control driver or ground.

In the absence of a reference electrode, the electrodes must be conductive to the solution, that must couple to the Fermi level of the solution, e.g., employ a redox compound such as ferriferrocyanide, and must be conductively coupled to the control driver.

For an amperometric determination (redox), a reference electrode is required and a conductively coupled control electrode is required.

Where the capacitive mode is employed in conjunction with a reference electrode, a conductive control electrode is employed for each site, where each electrode may be energized independently or frequency coded; or a capacitive control electrode is employed where a reference or separate control electrode controls the potential, $\Psi$. In the latter configuration, the conductive electrode may be capacitively coupled to the modulation source or the conductive electrode coated with a thin insulating surface layer may be coupled to the modulating source. Without a reference electrode, the configuration has the conductive electrode conductive to the solution, coupled to the Fermi level of the solution (ferroferricyanide), and conductively coupled to the control electrode driver.

Desirably, a reference site on the working electrode is used with all the configurations to reduce drifts resulting from thermal, electrode or other changes with time. Various physical embodiments may be employed involving flow cells and wicking, for the transport of liquids. Devices may be equipped with membranes which may serve to concentrate components of the assay, e.g., cells or particles, where the membrane may be pressed against the working electrode during measurement.

A thread, wire, tape or other continuous support may be employed for performing chemistries external to or internal to the measurement cell, where the production of the signal occurs in the measurement cell. The extended support can be provided in a roll which is fed to a reel in a continuous or interrupted manner.

In addition to the elements described above, the construction of the device will involve a single or a plurality of inlet and outlet ports, and means for varying the volume of the cell. Means which may be employed include pistons, diaphragms, cams, bellows, elevated gas pressures, or the like.

In FIG. 1, is depicted an exemplary electrochemical cell employing a photoresponsive working electrode, shown in schematic cross-sectional view, while detailed cross-sectional views of cell 10 are shown in FIGS. 2 and 3. Cell 10 includes container 12, piston 14, working electrode 16, and transparent support plate 18, which supports the working electrode. A light source 20 illuminates the working electrode 16 through support plate 18. The transparent support plate 18 may be shaped so as to focus the light at a site on the surface of the working electrode 16. While only one light source is indicated, there may be present a plurality of light sources, each light source illuminating a particular area of the working electrode 16. Access ports 22 and 24 are provided, which can serve as an inlet our outlet, depending upon the particular need.

Piston 14 can reciprocate so as to be in a generally raised or "up" position (FIG. 2) or generally lowered or "down" position (FIG. 3). The container 12 is in sealing engagement with the working electrode 16. The container has access areas 30a and 30b as concavities in the container providing small chambers into which fluids can be introduced or withdrawn, where the small chambers have communication with the larger chamber 40. Additional small chambers may be provided with channel access through the chamber container to the outside for introducing or removing various solutions or providing access to one or more reference or other electrodes.

In FIGS. 1–3, the container is provided with O-ring 32 to prevent leakage. Similarly, piston 14 is sealingly engaged with the walls of container 12 by means of O-ring 36.

The volume in chamber 40 is controlled by the movement of piston 14 from the up position, which allows for a relatively large volume in the chamber, to the down position where the piston bottom 42 is in close juxtaposition to the working electrode upper surface 44. The bottom 42 and upper surface 44 will have a substantially uniform separation of distance, "D" in the down position and distance "d" in the up position.

While for the most part, the piston bottom 42 and upper surface 44 are flat, other surfaces are permissible, such as cylindrical, spherical, incline, or the like. The separation between the piston bottom 42 and upper surface 44 or sample depth may be as small as 0.1 $\mu$m and will usually not be more than about 5 mm, usually not more than about 1 mm, and frequently less than about 0.05 mm.

The piston 14 may be formed of any of a variety of rigid materials, so long as the central-electrode 70 which is positioned on the piston bottom 42 can be electrically connected to a circuit or ground. The electrode material should be chemically inert to the environment to avoid signals associated with events other than the measurement of interest, typically metal-oxygen reactions. If desired, the piston 14 may provide for a light source, so as to irradiate the working electrode 16 through the sample.

The particular manner in which the reciprocating movement of the piston 14 is controlled is not critical, there being numerous mechanical, electrical, and pneumatic techniques for defining precise movement of a piston. In the subject figure, a stop collar 38 is employed to control the separation in the down position.

Light source 20 may be any of a variety of light sources, such as incandescent lamps, hollow cathode lamps, gas vapor lamps, light emitting diodes, lasers, semiconductor diode lasers, tunable dye lasers, and the like. Desirably, light source 20 will provide for a time-varying light signal. For example, the intensity of light can be modulated electronically according to well known techniques to vary the output of light source 20 sinusoidally or in other patterns at a determined frequency in the range of about 10 Hz to 100 kHz, usually 100 Hz–50 kHz, more usually 1–20 kHz, during the period of irradiation. Alternatively, where the light source cannot be modulated, the intensity of light delivered to the working electrode 16 may be modulated by a mechanical means, such as choppers, shutters, or the like. Where the intensity of the light source 20 is modulated, the electronic signal derived from a photoresponsive working electrode 16 can be selectively detected or measured with synchronous frequency and/or phase detection techniques, frequency selected electronic filtering, gated amplifiers, or the like, according to known techniques.

As desired, the light may also be limited to a selected wavelength or range of wavelengths by employing a light source providing the desired wavelength range, e.g., lasers, light-emitting diodes, etc., or with broadband sources, the wavelength can be selected with, for example, gratings, prisms, filters, monochromators, or the like. The choice of wavelength range may relate to the type of measurement or experiment to be performed or particular wavelength ranges to which the photoresponsive electrode is sensitive.

While working electrode 16 is shown as a monolithic wafer, or single continuous plate, the working electrode can have varying configurations. Rather than a single wafer, a plurality of chips may be employed, which may or may not be in electrocommunication with each other. Thus, each of the chips may be electrically insulated one from the other and connected to a common circuit or different circuits for detection. The same or different materials may be used for the plurality of chips, so that the working electrodes may respond differently to the same environment. The same electrode may be processed differently at different sites so as to provide a varying response.

In carrying out a determination using the device depicted in FIGS. 1–3, the sample may be introduced into inlet port 52 with the piston in the up position where channel 52 accommodates syringe needle 63, which exits into small chamber 30b. The sample solution may be introduced by means of syringe needle 63 into chamber 40, where any reaction for the assay determination may be carried out. One or more solutions may be introduced as appropriate for the determination. If desired, after an addition, the reagent may be expelled by lowering piston 14 so as to expel the solution through channel 54 to the outside. After the appropriate reaction has occurred to provide the binding of a label to surface 44, piston 14 may now be lowered as depicted in FIG. 3 so that the distance between the control electrode 42 and the upper surface 44 of the working electrode 16 is now D. By irradiating the working electrode 16 with light from light source 20, a signal may be obtained correlating with the nature of the label in close proximity to the electrodes 16 and 42. The amount of label and the effect the label has on the working electrode conduction band may be related to the amount of analyte.

An alternative embodiment of the subject invention is depicted in FIG. 4, where the electrochemical cell 10 has chamber 40 with check valves 60 and 62 providing for ingress and egress to chamber 40. As piston 14 is raised, fluid flows into the chamber 40 and, conversely, as piston 14 is lowered, fluid is expressed through check valves 62 from chamber 40. The check valves can be any of a variety of valves, such as ball valves, hinge valves, and the like. By reciprocating piston 14, solutions can be continuously introduced and expelled in a serial manner, allowing sufficient time for the various procedures to occur, such as reaction, wash, reversal of complex binding, and the like. Thus, by providing for an automated cycling, one can provide for alternating sample, wash and treatment solutions in conjunction with the reciprocating movement of piston 14.

The subject device will have at least the working and control electrodes, but desirably will include a reference electrode (not shown) such as a standard calomel electrode, silver-silver chloride electrode, or other electrode which provides for a standard potential. The reference electrode will be mounted to provide for electrical contact with the sample solution. The reference electrode may be distant from the sample solution, providing for a bridge, or may be in direct contact with the sample solution, for example, through a channel such as channel 54. Suitable reference electrodes and mounting techniques may be found in, for example, U.S. Pat. No. 4,020,830.

The working electrode 16, will desirably be a photoresponsive electrode, which includes an irradiation surface 66 and a solution confronting surface 44 on opposite sides of the photoresponsive electrode 16. As already indicated, where the piston provides for a light source, the irradiation surface and solution confronting surface may be the same.

The other electrode, in the three electrode configuration, is an electrochemically inert controlling electrode 70, mounted preferably on the opposite side of sample region 40 from working electrode 16 as the bottom of piston 14.

Photoresponsive working electrode 16 is unpolarized or polarized with respect to a suitable controlling electrode 70. Photoresponsive electrode 16 can be polarized with either a reverse or forward bias, where current is either inhibited or allowed to flow through an electrically communicating nonmetallic medium, usually a polar fluid medium, e.g., an aqueous medium. Suitable methods and circuits for polarizing photoresponsive electrode 16 are known, as, for example, in International Patent Publication No. WO85/04018.

Photoresponsive electrode 16 is preferably a semiconductor electrode from which an electrical signal, measured with respect to the reference electrode, is inducible or variable, depending upon the effect of irradiation and upon the surface potential of surface 44 of photoresponsive electrode 16. Photoresponsive electrode 16 may be a wafer or coating mounted to or coated on a portion of surface 66 of base 18.

Photoresponsive electrode 16 can be connected to appropriate electrical circuitry (e.g., FIG. 5, discussed below) with a thin conductive, for example, metallic layer coated on surface 66 of supporting plate 18 or with a lead passed through supporting plate 18, as will be known in the art. In the configuration of FIGS. 2 and 3, irradiation surface 66 of photoresponsive electrode 16 confronts supporting plate 18. the electrical signal obtained upon illumination of photoresponsive electrode 16 will be affected by the processes and components of the solution contained in the sample region 40, and can be used, as described more fully below, to determine the presence, concentration, or other characteristics of a substance in the solution or other solution property of interest.

As indicated, the working electrode 16 will be a semiconductive material, which may also be photoresponsive. Semiconductive materials include such materials as silicon, gallium arsenide, gallium selenide, aluminum gallium arsenide, or the like. The semiconductive material will be either of the p- or n- type and, as appropriate, may be intrinsic or may employ such dopants as boron, aluminum, phosphorus, arsenic, antimony, or the like. The degree of doping may be varied widely, there being a wide variety of commercially available doped wafers which can be used. The concentration of the dopant will normally vary empirically in order to provide the desired photoresponse, frequently being a matter of convenience, and will generally range from about $10^{10}$ to $10^{20}$ atoms/cc; usually for silicon the rating will be about 5–20 ohm-cm. Photoconductive materials include chlorogallium phthalocyanine. Rieke and Armstrong, *J. Am. Chem. Soc.* (1984) 106:47–50.

Various electrical circuits may be used to measure changes in photoresponsiveness of phororesponsive electrode 16 which result from changes in the state of an incremental portion of the solution. One example of such a circuit is described below in conjunction with FIG. 5. These electrical circuits may primarily measure changes in phototresponse which include photopotential and, photocurrent, or combinations thereof. Circuits will be chosen so as to provide maximal sensitivity for detecting small changes in the state of the solution. These measurements will generally be referred to as the photoresponse.

The observed signal from the circuit can be a result of the change in direct current, alternating current, or the effect of a direct current on an alternating current.

Where wafers are used for the working electrode 16, they may come in a variety of sizes and shapes, varying from chip size, which may have its largest dimension of about 0.1 mm. or wafer size, which may be 100 mm, more usually not more than about 75 mm in its largest dimension. A photoresponsive electrode will usually have at least one smooth surface or smooth portion of a surface, desirably flat, which will serve as the irradiation site and, in a preferred photoelectrical cell, be arranged for maximum efficiency of irradiation from a light source. The wafer may be round, rectangular, elongate or the like. The thickness of the wafer will generally be not more than about 1 mm. usually less than about 2 mm, and generally not less than about $0.05\mu$, usually not less than about 0.1 mm. being in the lower portion of the range when the irradiation surface is opposite the sample region.

The sample confronting surface 44 of photoresponsive electrode 16 may be modified by being reacted with a variety of substances, including, for example, various physiologically active proteins, such as membrane proteins, antibodies, enzymes, ligands, etc. or other substrates, to modify selectively the desired response of the photoresponsive electrode. Alternatively or in combination, the sample confronting surface 44 may be reacted with a wide variety of organic silanes, particularly halides or esters, which can provide for an organic coating of the surface. Methods and types of coatings which may find application are described, for silicon surfaces, in International Patent Publication No. WO83/026669 incorporated herein by reference. Such coatings can be used alone or in combination with other functional groups which may have an appropriate polarity, chemical nature, or reactive characteristic and may include, for example, carboxylate, phosphate, ammonium, carboxylate esters, phosphate mono-, di-, or triesters, and the like. Reactive groups so bound to the surface of the photoresponsive electrode may be further modified by reactions with proteins, enzymes, monoclonal or polyclonal antibodies, enzyme substrates, coenzymes, or the like. Where hydrocarbon radicals, particularly aliphatic groups of about 6 to 24 carbon atoms, either saturated or unsaturated, are attached to the surface of the photoresponsive electrode, a second layer may be employed to provide for a bilayer membrane. Alternatively, lipids forming stable lamellar membranes may be employed for both layers, avoiding covalent bonding to the surface. Illustrative groups include phospholipids, sphingomyelins, gangliosides, cholesteric compounds, phosphatidyl inositol, acylglycecols, waxes, and the like, where the different groups, particularly cholesteric compounds, are used in mixtures.

Various other materials may be used in conjunction with sample confronting surface 44, which materials may be bound either covalently or noncovalently, or held mechanically in place adjacent to the solution confronting the surface. The materials may be naturally occurring, or synthetic, or combinations thereof. These materials include porous films, generally of from about 0.25 to 50 mil in thickness, normally being polar materials, such as nitrocellulose, partially hydrolyzed polyvinyl acetate, polyacrylates, proteins, polysaccharides, e.g., agarose, cellulosic materials, e.g., filter paper, and the like. These layers may have independent integrity or rely on the photoresponsive device for support.

The photoresponsive electrode may have the sample confronting surface 44 and irradiation surface 66, each having a surface area of about 1 mm$^2$ to about 50 cm$^2$, more usually about 5 mm$^2$ to 25 cm$^2$. The extent of the irradiation surface 66 and also of the involved sample confronting surface 44 are chosen to be commensurate with the physical practicalities of the photoelectrochemical cell 10, e.g., the size of the sample region, the area which is illuminated, etc. Generally, where sample confronting surface 44 and irradiation surface 66 of Photoresponsive electrode 16 are not the same surface, the two surfaces may or may not be approximately coextensive.

Irradiation of photoresponsive electrode 16 on irradiation surface 66 of the electrode may be on either the side of photoresponsive electrode 16 confronting the sample region 40 (solution-confronting surface 44 of photoresponsive electrode 16) (e.g., FIG. 4) or on the side of the photoresponsive electrode opposite from the sample region 40 (e.g., FIGS. 2 and 3). However, where irradiation surface 66 is on the side of photoresponsive electrode 16 opposite to the sample confronting surface 44 (FIGS. 2 and 3), the wafer or coating comprising the photoresponsive electrode 16 will usually be thin, on the order of the minority carrier diffusion layer or less, usually about 0.01 to 5 mm. Normally, in this situation, the thickness of the photoresponsive electrode 16 will be from about $0.05\mu$ to 0.5 mm.

In the embodiment of electrochemical cell 10 shown in FIGS. 2 and 3, counterelectrode 70 may be formed from an inert, electrically conductive material, e.g., a noble metal, such as platinum, gold, iridium, rhodium, or the like, which is electrochemcially inert to the medium of interest and does not react with oxygen under the conditions of the determination.

The controlling electrode 70 may also be fabricated to have surfaces in contact with the sample solution which are inert semiconductor materials such as, for example, Si, GaAs, etc. Controlling electrode 70 may also be formed entirely or in part with composite materials such as, for example, platinum impregnated Teflon. In embodiments in which it is desirable that the controlling electrode 70 be transparent, as for example, those embodiments in which it is desirable to illuminate sample region 40 and/or photoresponsive electrode 16 through piston 14 of FIGS. 2 and 3, controlling electrode 70 can be formed to be a layer on the piston bottom 42 with a suitable hole or transparent area for illumination of photoresponsive electrode 16. Alternatively, in such embodiments, a translucent, semitransparent, or transparent controlling electrode 70 could be used; controlling electrode 70 could then, for greatest efficiency of both illumination and electrode response, cover all of bottom 42. Suitable light-transmissive controlling electrodes could be formed from a partially metallized thin bottom 42, as with gold, platinum, or the like.

Alternatively, controlling electrode 70 could be comprised of a transparent or partially transparent semiconductor material of, for example, tin oxide, indium oxide, titanium dioxide, or strontium titanium trioxide. Controlling electrode 70 could also be formed from a coating of a light-transmissive polymeric semiconductor on bottom 42; suitable polymeric substances that may find use include polyacetylene, doped polyacetylene, metal doped polyacrylonitrile, polypyrrole, polyalkadienes, and the like. Suitable dopants may include iodine, sulfuric acid, arsenic pentafluoride, antimony pentachloride, nitro antimony hexafluoride, and the like; the conductivity of such polymeric substances can also be modified using electrochemical oxidation. The material of controlling electrode 70 will be chosen to be compatible with oxygen and the fluid medium of interest.

One suitable circuit for the measurement of the photoresponse or other electrical signal generated with electrochemical cell 10 involves automatically varying the potential between controlling electrode 70 and working electrode 16 so as to maintain a constant amplitude sinusoidal current through controlling electrode 70 in response to sinusoidal irradiation of irradiation surface 66 of working electrode 16. Thus, variations in the chemical environment neat working electrode 16 can be determined by measuring the potential required to maintain a constant current. This measurement scheme is referred to as the constant amplitude mode.

A second suitable circuit fop the measurement of the photoresponse or other electrical signal generated with electrochemical cell 10 involves sweeping the potential between controlling electrode 70 and working electrode 16 and measuring the amplitude of the alternating current through the circuit, where the current is induced by sinusoidal irradiation of surface 66 of working electrode 16. The array thus produced, applied potential vs, photocurrent amplitude, is analyzed with digital electronics to determine the applied potential which corresponds to the point of maximum slope on the plot of photocurrent amplitude versus applied potential. This potential is dependent in a quantitative manner on variations in the chemical environment near working electrode 16. This measurement scheme is referred to as the constant potential mode.

A block diagram of an exemplary circuit is shown schematically in FIG. 5, which shows silicon wafer working electrode 16, controlling electrode 70, and reference electrode 78. Potentiostat 74 controlls the potential between aqueous solution 84 and working electrode 16 by monitoring solution potential through reference electrode 78 and applying the necessary potential to controlling electrode 70. Alternating current ammeter for 76 measures the alternating current through working electrode 16 and outputs a potential proportional to the amplitude of this current to output 80. This signal is used in the constant potential mode. In this mode switch 86 would be open. When switch 86 is closed a feedback loop to potentiostat 74 is formed which allows potentiostat 74 to maintain a potential from solution to working electrode 16 such that a constant photoinduced AC current is maintained through working electrode 16. In this constant amplitude mode potentiostat 74 provides an output 82 which provides a voltage proportional to the potential from solution 84 to working electrode 16.

Where capacitance is employed as the electrical response, the change in capacitance can be determined from the alternating current resulting from potential modulation superimposed on a lower frequency potential sweep.

A description of a capacitance signal may be found in U.S. patent application Ser. No. 768,977 incorporated herein by reference.

As already indicated, the photoresponsive electrode may be the bottom surface of the piston or may be the bottom of the sample chamber, so that the controlling electrode will remain opposite the photoresponsive working electrode. Depending upon the light transmissive nature of the electrodes, the light may be directed by various means, such as optical fibers, light guides, or the like to either surface of the photoresponsive electrode, the surface in contact with the sample, or the opposite surface of the photoresponsive electrode.

In some instances it may be desirable to have a second light source, where the two light sources may have different wavelengths. By modulating the two sources of light differently, for example with different frequencies, the electrical signal derived from the photoresponsive electrode resulting from the two light sources may be separated by suitable demodulation, filtering, synchronous detection, or other technique.

An alternative embodiment of the invention is depicted in FIGS. 6 and 7, where an expandable or resilient material is employed, which allows for introducing the sample with expansion of the resilient material, allowing the reaction to occur, followed by expulsion of the sample material to reduce the volume to carry out the determination. This embodiment is found in FIGS. 6 and 7, where device 100 includes a flexible cover 102, a spacer 104, which serves as walls for the sample chamber, a baseplate 106, which serves as the floor of the chamber, a light source 108, and inlet channel 110, and outlet channel 112. The flexible cover may be of any convenient material which is able to expand and contract under pressure and release of pressure. The inlet 110 may be connected by any convenient means to a source of liquid for introduction into the chamber 116, while the outlet channel 112 may be Joined to any convenient waste receptacle.

The spacer 104 is selected to provide the desired depth of the sample, and serves to control the volume of the sample during the determination. The spacer 104 will be about 0.1 mm to about 1 mm, usually less than about 0.5 mm. thick. The flexible cover 102 may be of any elastomeric material, which can be doped, so as to act as the controlling electrode. Various conductive materials can be employed as the flexible cover 102. A working electrode 114 may be coated onto baseplate 106 so as to be transparent to allow for light transmission to flexible cover 102. A lead can be coated on to baseplate 106 to extend under spacer 104 and connect working electrode 114 to an external circuit. The flexible cover may also be connected to the external circuit by appropriate leads, employing a circuit similar to the circuit previously described.

The next embodiment is depicted in FIG. 8 and schematically depicts a device referred to as the cartridge device. The cartridge device 120 has a feed spool 122 and a takeup spool 124. The carrier material on the feed spool can be any of a variety of materials which are porous and/or absorbent and may include perforated mylar, filter materials, cotton or NYLON threaded materials, or other materials capable of forming a film, thread, or the like, which may support a continuous or intermittent porous or absorbent layer. The material on the feed spool serves as a carrier for the chemistries to be carried out and will be selected so as not to interfere with the chemistries, but rather to provide the desired characteristics necessary for the assay determination.

The carrier material is fed through first guides 126, which serve to guide the carrier, as well as preventing any solution from escaping from sample chamber 128. In the subject embodiment, the carrier is depicted as passing through a sample solution. Alternatively, a syringe could be present which could put droplets of the sample onto the carrier at designated positions, where reagents may or may not be present. The sample may be dried by heating or other treatment to affix the sample to the carrier.

As depicted, the carrier has multiple coatings, only two coatings 130 and 132 being shown. These coatings may be present as spots, lines, pads, or the like, and may have one or more reagents present for interaction with the sample in the sample chamber. For example, the coating spots 130 and 132 may be two different antibodies or two different ligands or the like. One spot may be concerned with the sample and the other spot may provide a control.

A plurality of wash and reagent solution chambers 134, 136, and 138 may be employed, where in chamber 134, a plurality of guiding rods 140 are present. The guiding rods provide for an extended path of the carrier material, so as to extend the period of time in which the carrier material is maintained in chamber 134. Each of the wash and reagent solution chambers are separated by separator guide 144, which allow for continuous movement of the carrier material 142, but inhibit mixing of solutions from one chamber to the next. The separators 144 may be various silicon rubber or similar gaskets, elastomeric wheels, or the like, which may serve not only to inhibit leakage, but also to squeeze the carrier material, so as to minimize carryover from one chamber to the next.

After the carrier material has traversed the washing and reagent solution chambers, the carrier material enters into the reaction chamber 146. The bottom of the reaction chamber is depicted as having silicon wafer 148 as the working electrode. Piston 150 is conductive, desirably coated with a thin insulator, and serves a plurality of functions. In order to prevent leakage, piston 150 has O-ring 152 to seal against the loss of solution. Piston 150 has orifice 154 which provides for communication between reaction chamber 146 and piston chamber 156. Inside piston chamber 156 is reference electrode 158 connected by lead 160 to a circuit, not shown. LEDs 162a and 162b are positioned underneath silicon wafer 148 to illuminate the regions of the silicon wafer underneath the coatings 130 and 132 on carrier 142.

The entire device 120 can be organized so as to fit into a cartridge housing 164.

The piston 150 as the controlling electrode and the wafer 148 as the working electrode may be joined to a circuit to which the reference electrode 158 is also joined as described previously.

In carrying out an assay, the carrier material is spotted with a particular reagent, for example, an antibody. A plurality of spots may be employed, where the antibodies may be the same or different. The reagent spots are separated in accordance with the particular protocol, allowing for the introduction and removal of sample from the sample chamber 128. Thus, a pump can be employed for introducing the sample and, in accordance with a preselected schedule, expelling the sample, washing the sample chamber 128, and then introducing a new sample. The period of time in which the reagent spots remain in the sample chamber will be controlled by the rate of the uptake spool 124 and the length of the path of the reagent spot in the chamber. Of course, the uptake spool need not be continuous but may move intermittently where the time at various positions may vary in accordance with a predetermined schedule or a schedule associated with each determination.

In the illustrative method, the reagent spots are two different antibodies, where it is known that the sample contains only one ligand, so that the other spot may serve as a control or negative. The two spots enter the sample chamber and are allowed to react with any ligand present. From the sample chamber, the reacted spots move to a reaction chamber which contains monoclonal antibodies specific for an epitopic site on the ligand different from that to which the antibodies of the spots on the carrier bind. The residence time is extended by having the carrier move about the rods, so as to have an extended pathway in the reaction chamber 134.

From the reaction chamber 134, the carrier moves to a second reaction chamber 136, which contains an enzyme, e.g., urease conjugated to anti-mouse antibody, where the second antibody was a mouse immunoglobulin. Thus, any mouse antibody which binds to the ligand, providing a sandwich assay, will be bound by the conjugate, so that the amount of urease which binds to the carrier will be proportional to the amount of ligand that was in the sample.

From reaction chamber 136, the carrier moves to washing chamber 138, where any nonspecifically bound enzyme conjugate is removed from the carrier, so as to insure that the amount of enzyme present which is bound to the reaction spots on the carrier is specifically bound. From the wash chamber 138, the carrier then moves to the reaction chamber 146. The reaction chamber 146 contains substrate for the reagent for the enzyme. In the case of urease, this would be urea at a pH which is generally optimum for the enzyme, but the medium is relatively lightly buffered, e.g. less than about 50 mM, usually less than about 1 mM, typically 100 $\mu$M so as not to interfere with the change in pH upon the hydrolysis of the urea.

When the reaction spots move to the reaction chamber, they will be positioned over the LEDs 162a and 162b and may be halted there. The piston 150 is then pushed down, so as to press the carrier 142 against the wafer 148 and remove most of the liquid medium into which hydroxide ions would diffuse from the spots. The carrier material will retain a sufficient amount of the substrate, so that the enzyme reaction can proceed and, In the case of urease, the presence of the enzyme will result in a substantial change in pH.

By actuating the LEDs alternately, an increasing pH at one site as compared to the other site will indicate the presence of the ligand associated with the antibody at that particular site. Once the determination has been made, the piston may be raised and the uptake spool turned so as to remove the spent reactant sites from the reaction chamber and prepare the reaction chamber to receive the next reactant spots.

By having a relatively large volume of substrate in the reaction chamber initially, the small reaction which occurred at the reactant spots will be diluted out, so that a plurality of determinations can be made without having to change the substrate solution. In this manner, cartridges can be made which can be relatively small, fit into an apparatus which has the appropriate circuitry and machinery for moving the spools, and when the spools are spent, the cartridge may be discarded or reloaded, as desired. For continuous determinations, the various chambers can allow for flow through so as to have continous or intermittent replenishment of the solution.

Figure 9:
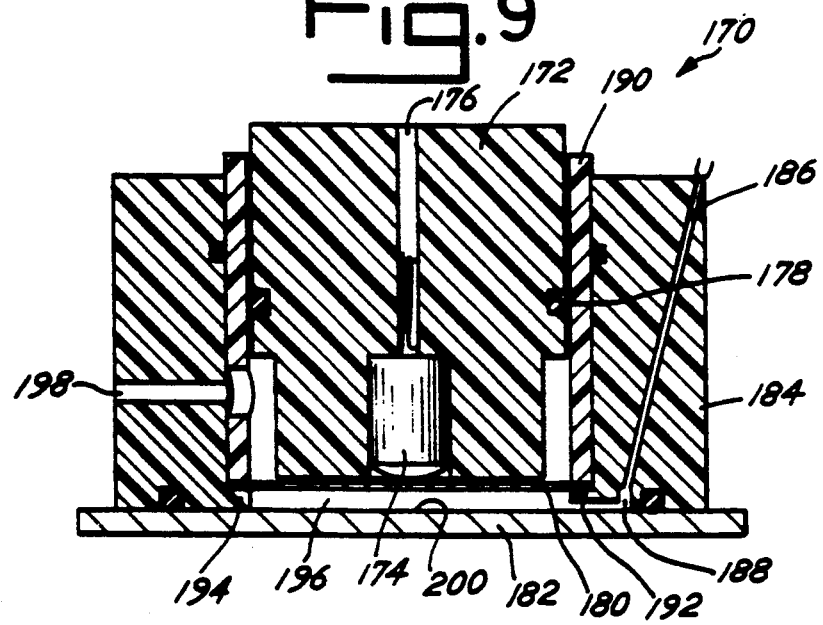
FIG. 9 is a diagrammatic view of a filter flow cell device.

The next embodiment in FIG. 9 is a filter flow cell. In this embodiment, one can concentrate a particle of interest, such as a cell, virus, membrane fragment, synthetic particle, or the like on a filter membrane, which can be positioned close to the working electrode, generally not more than about 100 microns. The filter flow cell 170 has piston 172 with controlling electrode 174 connected to an outside circuit by conductive rod 176. Leakage around the piston is prevented by O-ring 178. A filter membrane 180 is positioned between the controlling electrode 174 and the working electrode 182, which electrode is conveniently a silicon wafer. The housing 184 has inlet channel 186, which channel has exit port 188, which port is below filter membrane 180.

Cylinder 190 fits into housing 184 and serves to house piston 172 and position filter membrane 180 in conjunction with supports 192 and 194. The cylinder is removable from the housing, so that after each use of the membrane, the cylinder may be removed from the housing, the spent membrane discarded and a new membrane positioned on supports 192, 194 and locked into position by cylinder 190. Reaction chamber 196 may have varying volumes depending upon the movement of piston 172, the piston generally being in either an up position, during the reaction, and in a down position pressing filter membrane 180 down against working electrode 182 during the determination. Reaction chamber 196 has outlet channel 198, where excess liquid may be expelled from reaction chamber 196. Various O-rings are provided which need not be individually indicated to minimize leakage from the housing or through the cylinder.

Two cells may be placed in tandem, where the second cell receives the filtered medium from the first cell. The second cell need not have a membrane, but in order to provide an accurate reproduction of the system in the sample cell, a membrane could be included. By using the filtered medium for the control cell and a common circuit for the two cells, a difference in signals between the two cells should correlate with the presence of the analyte in the sample cell.

In carrying out an assay, one would introduce the sample through inlet channel 186 into chamber 196, with the piston in the raised position, so as to provide for a relatively large volume of fluid to pass through chamber 196 and exit through outlet channel 198. After the sample has passed through reaction chamber 196, additional reagent solutions, wash solutions, and the like may be passed through reaction chamber 196, where they may undergo a variety of reactions associated with the presence of the analyte trapped by filter membrane 180. The piston 172 may now be lowered to the down position, where it urges the filter membrane 180 toward the working electrode 182. The substrate solution may now be introduced through inlet channel 186 to fill chamber 196, so as to have the substrate solution in contact with the filter membrane, while the volume of the reaction chamber is low. To further reduce the volume of the chamber, by appropriate choice of the filter membrane material, one can bring the piston all the way down, pressing the filter membrane 180 against the surface 200 of the working electrode 182. In this manner, the determination can be carried out with a minimum volume, with the reagents in close proximity to the working electrode. Furthermore, the filter membrane retains its moisture during the measurement being surrounded by the medium.

As appropriate, one could provide for a reference electrode in the outlet port, so as to provide for a circuit as has been described previously. Where a photoresponsive electrode is employed, a light source will be employed or capacitive measurement can be made, due to the effect of the medium on a capacitive element in the silicon wafer.

Figure 10:
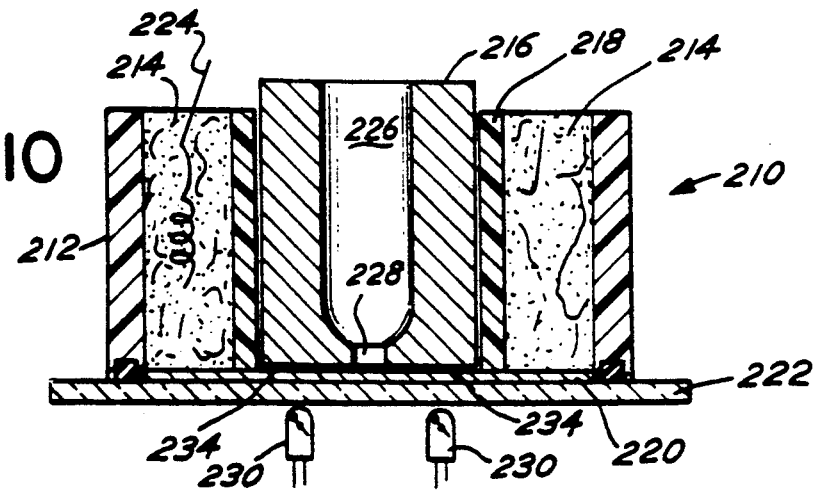
FIG. 10 is a diagrammatic view of a wicking device, with 10a being a plan view of the piston, 10b being a view looking upward at the bottom of the piston and 10c being a plan view of an exemplary filter membrane.

In the next embodiment as shown in FIG. 10, a wicking device is employed, which has many elements similar to the devices previously considered. Similar to the filter flow cell of FIG. 9, the wicking device 210 has a housing 212, a wicking material 214, and a piston 216 which also serves as the controlling electrode. Inner wall 218, serves as the piston chamber and acts to lock the filter membrane 220 in place proximal to the photoresponsive electrode 222. A reference electrode 224 is provided, which is in contact with the wetted filter membrane 220 through wicking material 214. O-rings are provided for inhibiting leakage. Piston 216 has reagent chamber 226 and orifice 228 through which reagent can contact filter membrane 220. Two LEDs 230 are indicated, which are merely illustrative of the fact that a plurality of LEDs may be used to illuminate specific sites of the silicon wafer in relation to different chemistries which may be impregnated in or be present on the filter membrane 220 at different sites, as depicted in FIG. 10c.

The various electrodes may be connected to the appropriate circuitry for determination of a change in the medium which changes the photoresponsive signal obtained from the signal wafer in relation to a reaction occurring at the surface of the photoresponsive electrode 222.

In FIG. 10a, the piston 216 surrounds the chamber 226 which terminates in orifice 228. Looking upward, the piston appears as a wall 216 having orifice 228.

In carrying out the assay, one would place the filter membrane 220 with appropriate chemistries at various sites. As depicted in FIG. 10c, six different chemistries are indicated by the differently positioned dots 232. Again, one could imagine each of the dots 232 having a different receptor, e.g., antibody, or a different ligand or combinations thereof. The dots 232 would be positioned so as to be under the cylinder 216.

In carrying out the assay, the sample solution, reagent solutions, and washing solutions could be added in accordance with the appropriate protocol, either consecutively or concurrently, depending upon the particular solution, where the solutions would pass through orifice 228 and extend under piston 216 into region 234, where the solution would be absorbed by the filter membrane 220. The media would then travel by means of capillary action through the membrane 220 to wicking material 214, where the wicking material would absorb the fluid permitting the addition of the next fluid. Each of the fluids would migrate through the same path, to be ultimately expended in the wicking material. The piston 216 may be fixed or preferably movable, so that it may squeeze the filter membrane 220 against the silicon wafer 222, so as to minimize the volume of liquid in contact with the silicon wafer 222. Each of the spots 232 may then be individually interrogated by sequentially irradiating the region underneath the spot with the related LED. In this manner, a plurality of determinations can be rapidly made. The device may be disassembled, the spent filter membrane 220 discarded, a new filter membrane introduced, and the process repeated.

An additional embodiment is depicted in FIGS. 11 and 11a which is referred to as a rigid filter device. In FIG. 11, device 250 has a fluted piston 252 which also serves as the controlling electrode. The base of the device is the working electrode 254, which may be conveniently a silicon wafer. Cylinder 256 houses the fluted piston 252 and is enclosed at the bottom with filter membrane 258. Device body 260 has inlet channel 262, into which the various samples, reagent solutions, and wash solutions may be introduced. The device body has O-ring 264 to provide a leak-proof seal with the working electrode 254. FIG. 11a is a plan view of the fluid piston 252 with a plurality of flutes 266. The flutes allow for escape of fluted from the chamber 268 defined by the device body 260 and the working electrode base 254.

This device operates in a similar manner to the device depicted in FIG. 9, except that the membrane may either be rigid and brittle or flexible, since the membrane need not be flexed to be pressed against the working electrode 254. In carrying out the assay, the sample solution may be introduced into chamber 268 through inlet port 262 and particles, such as bacterial cells, will be collected on filter membrane 258. A relatively large sample may be introduced into chamber 268 and pass through filter membrane 258. At the completion of the introduction of the sample, nutrient medium may be introduced, which has components which may result in a change in pH. The cylinder 256 may then be pressed down, the cylinder sliding within the walls of the device body 260, so that the membrane 258 is pressed against working electrode 254. The piston controlling electrode 252 may then be pressed down against the filter to minimize the reaction volume adjacent to the working electrode 254. A change in pH as a result of the metabolism of any cells collected on filter membrane 258 may then be detected.

The next device, as depicted in FIG. 12. is referred to as a diaphragm device. This device employs a diaphragm and air pressure for pumping solutions through a sensor and for reducing the volume in a flow cell without a piston. The device further demonstrates a configuration compatible with capacitive measurements, as well as photomeasurements. Employing separately wired controlling electrodes permits monitoring of discrete sites on a wafer without LEDs by modulating the potential on each of the controlling electrodes and measuring the resulting alternating current. Another feature of this device is the provision for a reference cell. Having two cells on the same piece of silicon allows for sample and reference readings to be multiplexed. The reference readings can be used to subtract drifts, such as thermal drifts in the reference electrode, silicon. electronics, or other component of the device, where temperature or other element may result in a change in signal unrelated to the sample. The common reference electrode insures the same solution potential in both the sample and reference cells.

In this device, the sample chemistry may be immobilized on either the controlling electrode or silicon surface in one cell, but not the other cell. All solutions would be pumped sequentially through the sample cell and into the reference cell and out the outlet port. By the proper sequential application of air pressure and vacuum to the two air pressure ports, the same solutions will be maintained in both cells in the same order for the same amount of time. Air pressure is applied to both diaphragms for reading. In this manner, the reference cell also controls for non-specific binding events or background signal.

The diaphragm device 280 depicted in FIG. 12 has first and second air plenum chambers 282 and 284 in housings 286 and 288, respectively. Fluid 290 is introduced through inlet port 292 so as to flow through reaction chamber 290, conduit 292, and into control reaction chamber 294. Fluid may be expelled through outlet port 295.

Valves 296 and 298 control the introduction and removal of fluid. A common reference electrode 300 sits in well 302 in contact with fluid 290. First and second air pressure ports 304 and 306 are provided to control the height of the controlling electrode support for pumping and reading.

Insulative controlling electrode supports 308 and 310 are connected at their peripheries to diaphragms 312 and 314, which diaphragms completely surround the electrode supports so as to divide air chambers into a fluid region 316 and an air region 318. In each chamber a plurality of controlling electrodes 320 are mounted on controlling electrode supports 308 and 310 and connected to a circuit not shown, by leads 322. Lead 324 connects reference electrode 300 to the same circuit.

For each controlling electrode 320, an LED is provided so as to interrogate a particular area of working electrode 326, which area confronts a particular region of the working electrode 320. In FIG. 12a, a cross-sectional view of the diaphragm and controlling electrode assembly is depicted where the concentric flutes of diaphragm 312 are depicted by the various rings and the controlling electrodes 320 are supported by support 308.

In FIG. 13 is depicted a device employing a strip dipstick which may be used for a plurality of determinations, by having a variety of different chemistries associated on the strip in the appropriate spatial relationship. In the device, at each site a piston is employed for pressing the porous strip against the surface of the working electrode. The chemistries may be present on a single porous layer, or may be individual elements supported on a porous or nonporous support. In this manner, the various steps of the assay may be carried out external to the device, followed by introducing the strip into the device, where it is immersed into an appropriate solution which results in the production of a product which will affect the observed signal.

The strip measuring device 340 has housing 342 with chamber 344 containing the development solution for producing a product which provides a signal. The strip 348 is introduced through receiving port 350 and channel 352 into chamber 344. A plurality of controlling electrodes 354 are positioned so as to align with the sample and/or reference sites for the determination. A semiconductive electrode 356 serving as the working electrode serves as one wall of the chamber 344 and is held in place by gasket 357. Housing 342 includes reference electrode well 358 into which can be introduced the reference electrode, not shown, so as to be in electrical contact with the developing solution. This reference electrode chamber is fitted with fritted disk 359 separating the reference electrode well 358 from channel 360. Conveniently, the well 358 may be filled with 1 M KCl and use in conjunction with an Ag/AgCl reference electrode. Channel 360 exits at port 361 fitted with valve 364. Piston cylinder rod 364 fits into well 366, so that the pistons may extend down into well 344. A wire coil 368 surrounds cylinder rod 364 and serves to move controlling electrodes 354, so as to press strip 348 against the working electrode 356. The piston 364 seals well 366 with O-ring 374. In the particular embodiment, the controlling electrodes 354 are connected by leads 372 to a circuit not shown. The piston rod 364 is fitted with collar 370 which covers the chamber 366.

The strip 348 has analytical pads 376 at one end of the strip which provide for the necessary reagents for interacting with the analyte and the components of the assay system.

In carrying out an assay, strip 348 would be combined with the sample and any necessary reagents to provide for the appropriate chemistries to occur at pads 376. The strip would then be introduced through port 350 into channel 352, where the strip would travel, so as to position pads 376 in well 344, which would contain an appropriate reagent. For example, if the assay protocol involved binding of an enzyme to a pad, then the well could contain the substrate.

Piston 364 would be present in chamber 366, with the cylinder in the retracted position, so that the controlling electrodes are removed from the well 344. After the strip is positioned, the coil 368 may be activated, so as to drive the piston inward and press pads 376 against semiconductive electrode 356. Lights not shown, may be used to irradiate the opposite side of semiconductive electrode 356 at different times, where the irradiating light source is positioned so as to be immediately opposite a pad site. By employing circuits which have been previously described, the effect of the enzyme product on the surface potential of the semiconductive electrode may be determined and related to the amount of analyte in the sample medium. Coil 366 may then be energized so as to retract cylinder rod 364. Strip 348 may then be removed from the housing 342 and, the well 344 may be washed, if necessary, and be prepared for the next test.

A study was made of the effort of various volumes on the sensitivity of the device in detecting changes in pH as a result of urease catalysed hydrolysis of urea. A device comparable to the device of FIG. 1, having the following specifications was employed: p type Si wafer 20 ohm-cm, LED infa-red 870 nm, the piston was a 0.25" Kel F rod with a P+ rod present in the centre. A silver/silver chloride reference electrode was employed. Urease (2 mg/ml) in PBS) was incubated in the chamber for 10 min, whereby the enzyme binds to the semiconductor surface. After sequential washes, a urease substrate solution was introduced into the flow cell and the piston adjusted to various heights measured as the distance between the surface of the Si electrode and the end of the piston next to the silicon surface. With the electronic circuit in the constant amplitude mode, the change in bias potential was monitored as a function of time. For different piston heights, the piston was raised, fresh substrate introduced, and the piston height appropriately adjusted. The calculation of the rate of pH change was based on a 50 mV/pH unit as determined with standard buffers. Based on these determinations, changing the piston height from about $400\mu$ to about $14\mu$ resulted in an increase in the rate of change of pH of 1.5 pH unit/h to about 220 pH unit/h.

The next study was in a device generally depicted in FIG. 9 having specifications similar to those indicated for the previous experiment. The potential was measured as a function of time with the electronic circuit in a constant amplitude mode. The bacterial nutrient medium was introduced into the assay chamber and the signal was measured for 300 sec. to establish an instrument base line. Approximately $10^6$ E. coli were then flushed into the cell with the piston retracted followed by an addition of the same medium, the piston lowered and the signal followed for 300 sec., with the process being repeated, followed by a similar series using a bacterial medium containing times the buffer concentration. The data showed that multiple readings could be made on bacteria from a single introduction. In this manner, bacterial response to various media can be determined to determine the particular species or strain.

The next study used the device of FIG. 9, except no membrane was used. After incubating the assay chamber with 10 $\mu$g/ml urease in PBS for 5 min., excess enzyme was washed out and the potential measured as a function of time with the electronic circuit in the constant amplitude mode. Measurements were then made with a saline solution, containing 16 mM urea, with EDTA varying fromm 10 to 0.1 mM. All measurements were taken with the piston down. The different concentrations could be readily distinguished. Since it is not convenient to use buffers below 0.1 mM in concentration, the spacing between the electrode should be not greater than about 1 $\mu$m to enjoy full sensitivity.

In accordance with the subject invention, apparatuses and techniques are provided for performing sensitive assays, particularly where the analyte may be involved with very low concentrations or be present in extremely small amounts. Where the analyte can be concentrated by means of filtration, precipitation, agglutination, specific binding, combinations thereof, or the like, the signal resulting from the presence of the analyte can be confined to an extremely small area in extraordinarily small volumes. Thus, large amplifications can be obtained of a detectable signal, so as to be able to detect the presence of very low concentrations or absolute amounts of materials.

Of particular interest is the use of enzyme systems which provide a product which can be detected by a semiconductive element, which may be responsive to a photo or capacitive effect. The working electrode can be responsive to changes in pH, redox potential, or other detectable signal. The apparatuses can be miniaturized and be used for single determinations or a determination of a plurality of samples simultaneously, can be automated, or manually operated. By employing appropriate configurations, controls can be devised which closely mimic the sample medium, so as to provide for values substantially free of errors due to change in conditions. The subject apparatus and methods therefor find a wide variety of use in analytical laboratories, doctors' offices, homes and the like.

Although the foregoing invention has been described in some detail by way of illustration and example for purposes of clarity and understanding, it will be obvious that certain changes and modifications may be practiced within the scope of the appended claims.

What is claimed is:

1. An apparatus for detecting an analyte comprising a porous membrane with an enzyme affixed thereto, the apparatus comprising:

an assay chamber adapted to removably receive the porous membrane; a working electrode and a plunger means as confronting walls of the assay chamber;

means for moving the plunger means with respect to the working electrode from a distal position to a proximal confronting position so as to confine the porous membrane within 1 millimeter of the working electrode; and means for connecting the working electrode to an external circuit for measuring changes in an electrical characteristic of the working electrode in response to the enzyme on the porous membrane.

2. An apparatus as in claim 1 wherein, in the proximal confronting position, the plunger means is not more than 100 microns from the working electrode.

3. An apparatus as in claim 1, wherein in the proximal confronting position, the plunger means is within 14–400 microns from the working electrode.

* * * * *